United States Patent [19]
Pettit

[11] Patent Number: 5,955,030
[45] Date of Patent: Sep. 21, 1999

[54] APPARATUS FOR AUTOMATED DNA SEQUENCING

[76] Inventor: John W. Pettit, 7808 Potters Mill Ct., Derwood, Md. 20855

[21] Appl. No.: 08/686,581

[22] Filed: Jul. 26, 1996

Related U.S. Application Data

[62] Division of application No. 08/353,311, Dec. 5, 1994, Pat. No. 5,556,790.

[51] Int. Cl.$^6$ .................................................... G01N 21/64
[52] U.S. Cl. .......................................... 422/82.08; 436/86
[58] Field of Search .................................. 436/86, 89, 91, 436/94, 164, 171; 422/62, 82.06, 82.08

[56] References Cited

U.S. PATENT DOCUMENTS

| | | |
|---|---|---|
| 4,345,463 | 8/1982 | Wilson et al. . |
| 4,731,732 | 3/1988 | Warchol et al. . |
| 4,758,408 | 7/1988 | Krawetz et al. . |
| 5,068,798 | 11/1991 | Heath et al. . |
| 5,093,269 | 3/1992 | Leichnitz et al. . |
| 5,235,843 | 8/1993 | Langhorst . |

OTHER PUBLICATIONS

HPLC Analysis for 5–Methyldeoxycytidine in Cellular DNA Obtained Directly from the Culture Flask, by S.P. Thacker, et al. *Bio Techniques,* vol. 16, No. 2, pp. 218–219 (1994).
"Acousto–optic Tunable Filters Spectrally Modulate Light", by X. Wang, *Laser Focus World* (May 1992).
"Near–IR Acousto–Optic Tunable Filter", Crystal Technology, Inc. (Apr. 1993).
"Merging Spectroscopy and Digital Imaging Enhances Cell Research", by C.C. Hoyt, et al., *Photonics Spectra,* pp. 92–94, 96 (Nov. 1992).
"Biophysical and Biochemical Aspects of Fluorescence Spectroscopy," T.G. Dewey, et al. Plenum Press, (pp. 73–104), 1991.
"Acousto–optic Tunable Filters," by I.C. Chang, *Optical Engineering,* vol. 20, No. 6, pp. 824–829 (Nov./Dec. 1981).
"AOTF Overview: Past, Present and Future," by P. Katzka, Acousto–Optic, Electro–Optic, and Magneto–Optic Devices and Applications, *SPIE,* vol. 753, pp. 22–28 (1987).
"Large–Scale and Automated DNA Sequence Determination," by T. Hunkapiller, et al., *Science,* vol. 254, pp. 59–67 (Oct. 4, 1991).
"Mid–IR AOTF Design Goals" Crystal Technology, Inc., 3 pages (1992–1993).
"DNA sequencing: present limitations and prospects for the future" by B.Barrell, *The FASEB Journal,* vol. 5, pp. 40–45 (Jan. 1991).
"Genesis™ 2000 DNA Analysis System User Manual," Molecular Genetics Customer Support Group (Jan. 1992), pp. 3–6, 20–23, 28–29.
"Real Time Automated Simultaneous Double–Stranded DNA Sequencing Using Two–Color Fluorophore Labeling", by H. Kambara, et al. *Bio/Technology,* vol. 9, No. 7, pp. 648–651 (Jul. 1991).

*Primary Examiner*—Lyle A. Alexander
*Attorney, Agent, or Firm*—Blank Rome Comisky & McCauley LLP

[57] ABSTRACT

An automated DNA sequencing apparatus and method is disclosed in which a laser beam having a predetermined wavelength is sequentially focused on a plurality of lanes of DNA fragments migrating in a polyacrylamide gel and in which the DNA fragments have been tagged with fluorescent compounds. The resulting fluorescent light given off by each of the tagged DNA fragments is collected and diffracted by means of an acousto-optic tunable filter and the level of the diffracted light is then detected and analyzed in order to determine the DNA sequences of the analyzed DNA fragments. The automatic DNA sequencing system of the present invention operates under computer control to repeat a series of measurements of the fluorescent data at a multiple number of wavelengths such that the entire spectrum of fluorescence emissions from all four fluorescent tagged DNA bases can be measured at any number of wavelengths.

16 Claims, 5 Drawing Sheets

DETECTION AMPLITUDE VERSUS WAVELENGTH FOR ONE DATA RECORD

SYNTHESIZER FREQUENCY (WAVELENGTH)

EMISSION OUTPUT SPECTRA FOR FOUR TAGS T1-T4

WAVELENGTH

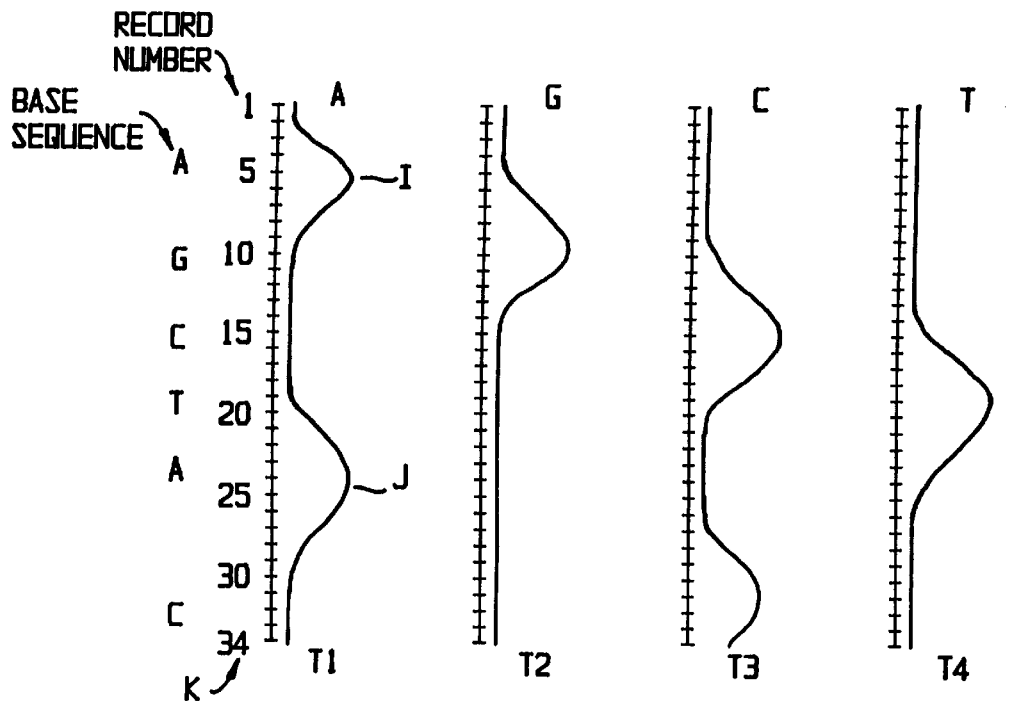
FIG. 3 DETECTION AMPLITUDE VERSUS RECORD NUMBER FOR EACH TAG T1–T4
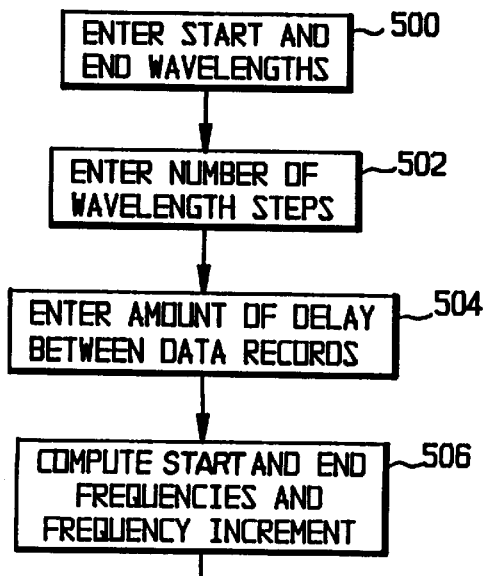
FIG. 5A
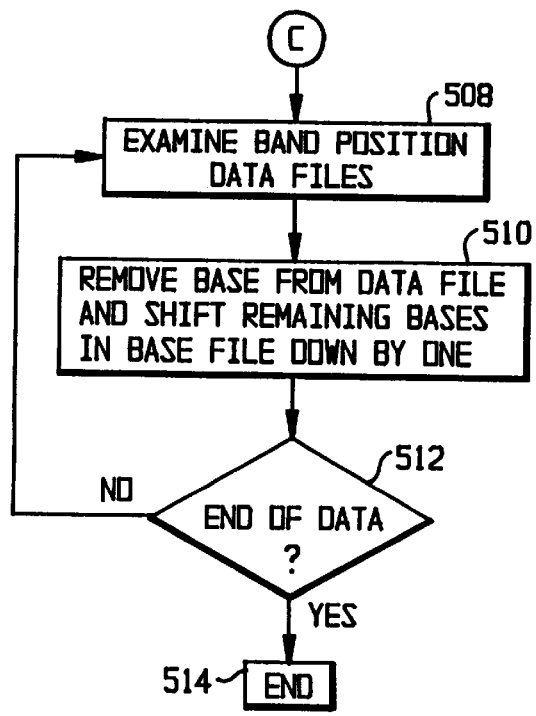
FIG. 5D

APPARATUS FOR AUTOMATED DNA SEQUENCING

This is a divisional of application Ser. No. 08/353,311, filed Dec. 5, 1994, now U.S. Pat. No. 5,556,790.

BACKGROUND OF THE INVENTION

The present invention relates generally to the investigation of the sequencing of DNA. More particularly, the present invention relates to a method of and apparatus for automating the sequencing of DNA which increases the rate at which DNA can be sequenced as well as improving the reliability and accuracy of the sequencing determination.

DNA sequencing is essential to the practice of biotechnology, genetic engineering and many other disciplines that rely on the need to determine the genetic information contained in DNA. The sequencing of DNA is the process of determining the sequence of nucleic acid bases that comprise a strand of DNA. There are four bases, denoted A for adenine, G for guanine, C for cytosine, and T for thymine, that comprise the DNA. The sequence of these bases uniquely describes each piece of DNA. Sequencing is a crucial step in genetic engineering and biotechnology, since it provides the precise code of genetic information contained in a sample of DNA.

DNA is double stranded and hence, the term base pairs is often used, since each base of one strand is opposed by its complimentary base on the other strand. There are an enormous number of bases that need to be sequenced in order to read a piece of DNA. Even a simple piece of DNA from a bacteria cell would likely comprise several thousand bases. The Human Genome Project, a large, multi-year, United States Government funded national project to sequence the DNA in humans, is attempting to sequence the approximately $10^9$ bases found in human DNA.

DNA sequencing is a very labor intensive process and, with the large amounts of DNA that are needed to be sequenced for the biotechnology industry to progress, methods and apparatus to automate this process are very desirable. Much has been written about DNA sequencing and genetic engineering and the reader is referred to the many references in this subject which will provide additional background information.

Two methods of DNA sequencing have been developed. The first is by Maxam and Gilbert, and is described in *Proc. Natl. Acad. Sci. USA* by A. M. Maxam and W. Gilbert, Vol. 74, page 560 (1977). The second method is described in *Proc. Natl. Acad. Sci. USA*, by F. Sangen, S. Nicklen and A. R. Coulson, Vol. 74, page 5463 (1977). Both of those methods involve performing a number of steps before the fragments of DNA are ready to be detected to yield a sequence. Those steps will not be reviewed here, as they are detailed in the two references noted above. Although the two techniques differ, eventually one arrives at four samples of DNA fragments that end at a given base. For instance, one sample contains fragments that end in base A; another other contains fragments that end in base G, and so forth.

The task is to separate those fragments by size and see what order they are in. If the shortest fragment in all of the four samples is one that ends in T, then the first base of the sequence is T. If the second shortest one ends in C, then the next base in the sequence is C, and so forth, until all of the fragments are separated in order of increasing length and the sequence is determined.

In order to perform this size separation and fragment detection, the first methods of manual DNA sequencing utilized polyacrylamide gel electrophoresis techniques to separate the fragments. Polyacrylamide gels have the ability to resolve fragments with a resolution of one base pair, and that resolution is necessary for sequencing. Each fragment is labeled with a radioactive element that typically gives off a beta particle, such as radioactive phosphorus, P-32. Each of the four samples are then separated in size in their own lane in the gel. The four lanes are typically side by side. After electrophoresis, a piece of x-ray film is placed next to the gel for a number of hours, often a couple of days, to expose the film with the radioactive emissions from the P-32 phosphorus. When developed, the fragments show up as dark bands on the film and the sequence can then be read from the order in which the bands appeared, from the bottom to the top of the film.

Automating DNA sequencing involves automating the process of detecting the fragments on the electrophoresis gel and then automatically determining the DNA base sequence from the sequence of detected fragments using the above algorithm implemented in a microprocessor. Because of the time needed to expose the x-ray film to the beta radiation of the P-32 phosphorus, and other considerations involving the use of radioisotopes, new methods of tagging and sequencing based on fluorescence were developed. See *Biophysical and Biochemical Aspects of Fluoresene Spectroscopy*, edited by T. Gregory Dewey, Plenum Press, 1997; "Large Scale and Automated Sequence Determination," by T. Hunkspillar, et al., *Science*, Vol. 254, pages 59–67 (1991) and "DNA Sequencing: Present Limitations and Prospects for the Future," by B. Barrell, the FASEB Journal, Vol. 5, page 40–45 (1991).

Fluorescence tagging of the fragments involves the attachment of a fluorescent compound, or fluorophore, to each fragment analogously to the attachment of the radioactive label to each fragment. These fluorescence labels were found to not adversely affect the process of gel electrophoreses or sequence.

Fluorescence is an optical method that involves stimulating the fluorescent molecule by shining light on it at an optical wavelength that is optimum for that molecule. Fluorescent light is then given off by the molecule at a characteristic wavelength that is typically slightly longer than the stimulation wavelength. By focusing the light at the stimulating wavelength down to a point on the gel and then detecting the presence of any optical radiation at the characteristic wavelength of light from the fluorescent molecule, the presence at that point of fragments of DNA tagged with that fluorescent molecule may be determined.

Two methods of implementing an automated DNA sequencing instrument are known in the art. One, reported by Smith et al., in *Nature*, Vol 321, pages 674–679 (1986), puts a different fluorescent tag on each of the four samples of fragments described above. Thus, the sample of fragments that end in the base A are tagged by one fluorophore; the sample of fragments that end in the base G are tagged by another fluorophore, and so on for the other two samples. Each fluorophore can be distinguished by its own stimulation and emission wavelengths of light.

In the Smith et al. method, all four samples are electrophoresed in the same lane together and the differences in their tags are used to distinguish them. That has the advantage that four separate lanes are not used, since the progression of fragments in different lanes is often not consistent with one another and difficulties often arise in determining the sequence as a result.

Another method, reported by Ansor et al., in *J. Biochem Biophys. Methods*, Vol. 13, pages 315–323 (1986) and Nucleic Acids Res., Vol 15(11), pages 4593–4602 (1987), uses one fluorescent tag for all fragments, but employs four separate lanes of gel electrophoresis in a manner that is similar to radioactive labeled sequencing. That approach has the potential disadvantage that four lanes, with different fragment migration rates caused by local temperature variations and other inconsistencies within the gel, could limit the reliability of the sequence determination.

Fluorescence tagging and the detection of natural fluorescence in molecules is a method of analytical chemistry and biology that is well known in the art. The methods described above have been developed for DNA sequencing by the creation of fluorescent tags that can be bound to fragments of DNA. The instruments used to detect fluorescence consist of the following parts. A light source with a broad optical bandwidth such as a light bulb or a laser is used as the source of the stimulating light. An optical filter is used to select the light at the desired stimulation wavelength and beam it onto the sample. Optical filters are available at essentially any wavelength and are typically constructed by the deposition of layers of thin film at a fraction of the wavelength of the desired transmission wavelength. The light that exits the optical filter is then applied to the sample to stimulate the fluorescent molecule.

The molecule then emits light at its characteristic fluorescent wavelength. This light is collected by a suitable lens and is then passed through a second optical filter centered at the characteristic wavelength before being brought to a detection device such as a photomultiplier tube, a photoconductive cell, or a semiconductor optical detector. Therefore, only light at the desired characteristic wavelength is detected to determine the presence of the fluorescent molecule.

The Ansorge method involves only a single light source, one stimulation optical filter, one fluorescent radiation optical filter and one optical detector. This apparatus is mechanically scanned across the gel to detect the presence of the fragment in the four lanes. Mechanical scanning is a disadvantage due to the slow rate at which the apparatus can be scanned, the alignment of the scanning and the repeatability and durability of scanning mechanisms.

The Smith method uses only one lane of electrophoresis, so it does not have the disadvantage of mechanically scanning the apparatus across the four lanes. However, there is a plurality of stimulation wavelengths and detection wavelengths that must be implemented. To do this, a mechanical wheel with four optical filters attached to it is rotated in the beam of the stimulation optical radiation. That selects in sequence the four stimulation wavelengths from the broad band optical radiation source. At the same time, a second mechanical wheel is fitted to the detection optical path to select the correct detection wavelength corresponding to the fluorophore being stimulated at the same time by the stimulation filters. Therefore, two mechanical rotating devices must be implemented, and operated in synchronism, in order to produce the correct result.

The complexities of such an electro-mechanical device with respect to maintaining synchronism and optical alignment are severe. This fact is pointed out in chapter 3 of the Dewey text, which is a review of automated DNA sequencing methods. A commercially available DNA sequencer that operates in a similar manner to that described above is available from Applied Biosystems, Inc., of Foster City, Calif., and is designated the ABI model 373A. Hunkpillar, in his April 1992 article in Science, points out that this DNA sequencer results in relatively long run times due to the mechanical operation of its four color optics. That is a big disadvantage in DNA sequencing which is overcome by the present invention.

Another prior art system for automated DNA sequencing was developed by DuPont of Wilmington, Del., and marketed as the Genesis 2000. It uses four fluorescent tags, one for each base, and runs them in a single lane. This system uses two fixed wavelength optical interference filters, each affixed to a photomultiplier tube light detector. The center wavelengths and bandwidths of these filters are chosen such that one of them is to the short wavelength side of the spectrum of wavelengths from the fluorescent tags and the other is on the long wavelength side. By looking at the ratio of the two detected signals, a determination can be made as to which base is being detected at a given time. For instance, if the signal from the short wavelength detector is much greater than the other one, it is inferred that the fluorescent tag with the shortest wavelength is present. Likewise, if the signal from the long wavelength filter is much greater, then the fluorescent tag with the longest wavelength emission is assumed to be present. If the two signals are close together in magnitude, then the fluorescent tag tending to that side of the two remaining ones in the middle, is assumed to be present. This technique, although workable, does not offer much resolution and it is reported by Dewey to no longer be commercially available.

Yet another prior art system for automated DNA sequencing has been developed by LI-COR, Inc., of Lincoln, Nebr., which is marketed as the Model 4000L Automated DNA Sequencer. This LI-COR system apparently operates using one florescent tag that emits radiation in the near infrared portion of the spectrum. The use of such a florescent tag is to produce less background florescence since the regular glass that the gel plates are made of, which is called "float glass" does not emit its own florescence in the infrared wavelength range. Float glass does, however, emit florescence in the visible wavelength range, which is a problem that has been noted in the prior art.

In addition, one method for reducing or eliminating the background florescence produced by the float glass when irradiated with the light in the invisible wavelength range is to "chop" the laser light. Such a method works because the florescence emissions of the constituents in the glass have long emission lifetimes, while the florescence tags themselves have short emission lifetimes. Thus, the interfering emissions from the float glass do not respond to the rapid chopping of the laser stimulation light and becomes a subtractible background signal. The present invention overcomes this background florescence problem in a more elegant and effective manner through the use of an acousto-optic tunable filter or acousto-optic modulator.

Recently, methods of preparing DNA fragments for sequencing using capillary hair techniques have been described. The present invention can be used with such methods of preparing DNA fragments for sequencing, as well as any additional methods or techniques of preparing DNA fragments, as long as fluorescent tags are used which can be caused to emit light in response to an impinging light beam.

SUMMARY AND OBJECTS OF THE INVENTION

In view of the foregoing, it should be apparent that there still exists a need in the art for a method of and apparatus for an improved DNA sequencer which has an extended range of the number of bases that can be sequenced in a single run compared to prior art devices. It is, therefore, a primary object of this invention to provide a method of and apparatus for DNA sequencing which utilizes solid state, digitally controlled equipment and is capable of operating several orders of magnitude faster than the known automated DNA sequencing technology.

More particularly, it is an object of this invention to provide an improved DNA sequencing system as aforementioned which utilizes solid state and reliable electronic components, which is not subject to mechanical failures and which does not require frequent alignment nor costly components.

Still more particularly, it is an object of this invention to provide an improved automated DNA sequencing system which uses a unique combination of electrically tunable optical filters which are employed to wavelength analyze the light emitted by the DNA fragments under intense laser light stimulation.

Another object of the present invention is to provide a reliable and relatively inexpensive automated DNA sequencing system for use in analyzing DNA bases.

Briefly described, these and other objects of the invention are accomplished by providing a solid state digitally controlled optical system which focuses a beam of laser light onto the gel containing multiple lanes of DNA fragments or into the capillary hairs containing such DNA fragments. In order to provide increased rejection of unwanted fluorescence and to stimulate fluorescence tags at their optimum wavelength to reduce stimulation of undesired fluorescence tags, the laser light may be chopped or modulated before it impinges upon the gel. The wavelength of the laser beam is such that it stimulates the fluorescent molecules with which the DNA fragments have been tagged. The fluorescent light given off as a result of the stimulation of the DNA fragments by the laser light beam is collected by a lens system and fed to a computer controlled acousto-optic tunable filter which is operated in such a manner that the fluorescent light entering the acousto-optic tunable filter is wavelength filtered such that light at the selected wavelength exits from the acousto-optic tunable filter at an angle of approximately 7–10 degrees from the main light beam exiting from the acousto-optic tunable filter. The acousto-optic tunable filter is controlled by means of a digital synthesizer which itself is controlled by the computer.

The selected light exiting from the acousto-optic tunable filter is diffracted in both directions relative to the main beam of light leaving that filter. Each or both of the diffracted beams at the desired selected wavelength are detected in order to provide an electrical measurement of the fluorescent emissions of the DNA fragments at the selected wavelengths. The output from the detector is fed to the computer and may be stored for later analysis.

The computer operates the instant automated DNA sequencing system by repeating a series of measurements of fluorescent data at a multiple number of wavelengths. In that manner, the entire spectrum of fluorescence emissions from all four fluorescent tags is then measured at any number of wavelengths. The fluorescence emissions measured at each of the selected wavelengths are then defined as a data record, from which the DNA sequences can be determined.

With these and other objects, advantages and features of the invention which may become hereinafter apparent, the nature of the invention may be more clearly understood by reference to the following detailed description of the invention, the appended claims and to the several drawings attached herein.

BRIEF DESCRIPTION OF THE DRAWINGS

FIG. 3 is a diagram of the band data generated using the system of the present invention showing the record number, base sequence and detection amplitude versus record number for each of the Tags T1–T4 from the data record shown in FIGS. 2A–2B.;

FIG. 5A is a diagram of a flow chart of a portion of the DNA sequencing software used for inputting parameters in connection with the operation of the apparatus of the present invention;

FIG. 5D is a diagram of a portion of the DNA sequencing software relating to determining the base sequence of a fragment of DNA used in connection with the operation of the apparatus of the present invention.

DETAILED DESCRIPTION OF THE PREFERRED EMBODIMENT

One of the objectives of the inventive DNA sequencing system is to extend the range and the number of bases that are sequenced in a single run. However, the migration rate of longer fragments does not differ by much when their length differs by only one nucleotide. In addition, when the fragment lengths reach the range of about 300 to 400 bases, the difference in migration distance in the polyacrylamide gels causes the bands to overlap and the sequence can no longer be determined. That is because it can not reliably be determined which band is further ahead of another when the detected signals blur together. Accordingly, a technique with greater resolution in detecting and determining the position of the bands within the gel would extend the range of the base sequence determination for a given run. A noticeable increase in that capability is of great utility to the biotechnology industry because of the time required to prepare and perform a gel separation.

The present invention utilizes a unique combination of electrically tunable optical filters, optical techniques and signal processing algorithms to significantly improve the ability to determine DNA base sequences over the prior art methods and equipment discussed above.

Figure 1:
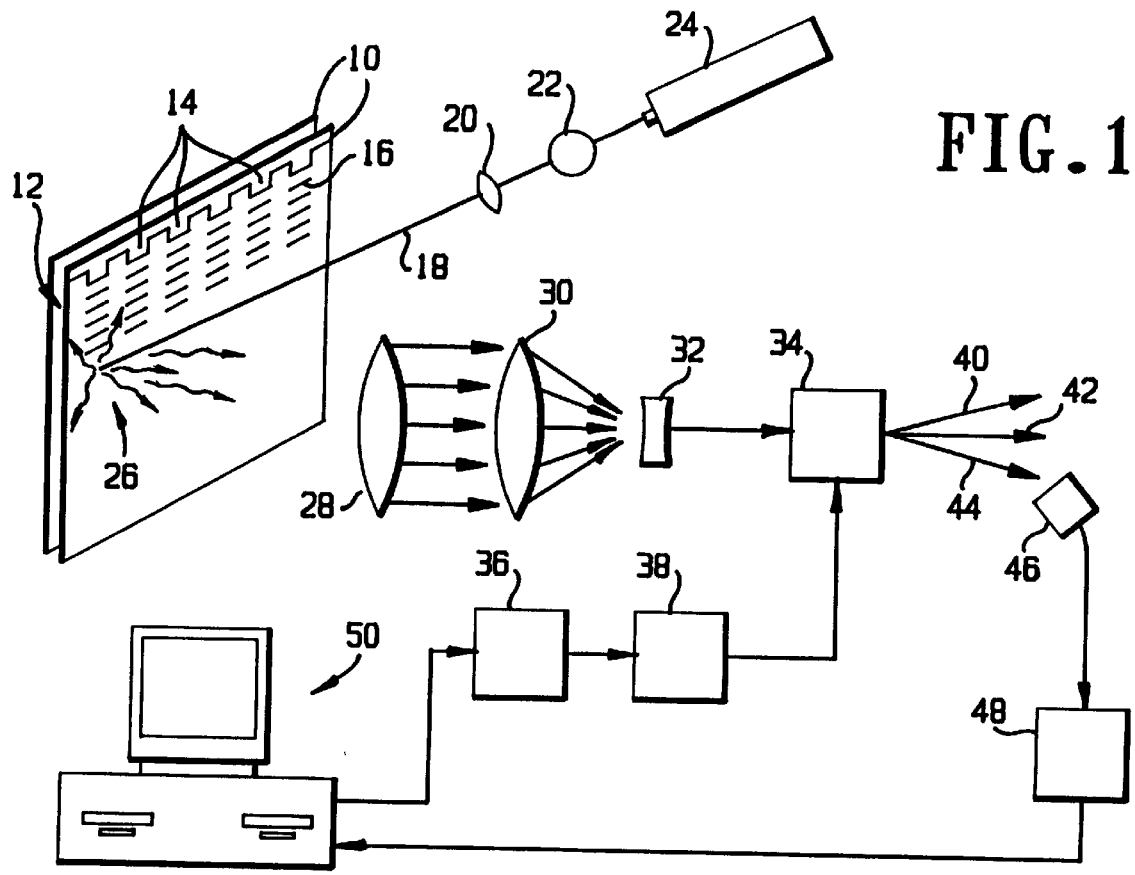
FIG. 1 is a schematic block diagram showing the apparatus of the present invention.

Referring now in detail to the drawings wherein like parts are designated by like reference numerals throughout, there is illustrated in FIG. 1 a diagram of the apparatus of the automated DNA sequencing invention which is used to generate and collect the fluorescent data from the bands of DNA in an electrophoresis gel. A pair of parallel glass plates 10 that hold the gel material 12 therebetween are illustrated in which a plurality of wells 14 in the gel which are used to load the tagged DNA fragments to create lanes are shown in which the DNA fragments 16 are migrating down the gel 12.

The gel 12 is loaded with fragments of DNA prepared in the prescribed manner by the sequencing techniques known in the art and described above and then tagged with four different fluorescent molecules, one for each base type. All four base types are then loaded into one of the plurality of wells 14 and become one lane on the gel.

A laser 24 generates a laser beam 18 which is capable of being moved in a horizontal direction in order to collect data from each of the many lanes 16 which are loaded in the same manner. Due to the compact size of the detection apparatus of the present invention as well as its speed of operation, many more parallel lanes can be run with the apparatus of the present invention than can be run using previously described methods and apparatus. The method of and apparatus for the present invention thus provides a distinct advantage over such prior art methods and apparatus, because parallel processing of the multiple lanes on a single gel 12 increases the throughput of the automatic DNA sequencing system.

As described above, the laser light source 24 generates the laser light which is used to stimulate the fluorescent molecules contained in the DNA fragments. The light from the laser 24 is first wavelength filtered by a fixed optical filter 22 which allows only light at the desired wavelength for stimulating the fluorescent molecules to pass through it. Alternatively, an acousto-optic tunable filter can be used in place of the fixed optical filter 22. As discussed hereafter in connection with FIG. 4, an infrared fluorophore can be utilized to decrease or eliminate the background florescence produced by the glass plates 10 which carry the gel material 12. As described more fully hereinafter, such background florescence can also be eliminated by high-speed modulation techniques. The thus filtered laser light 18 is then focused onto the gel 12 at the point where detection is to occur as a point source that is as small as can be attained. That is typically a diffraction limited point of light, which is produced by a lens 20.

The fluorescent light 26 given off as a result of the stimulation of the DNA fragments 16 by the laser light beam 18 appears to come from a point source due to the small spot size of the laser produced fluorescent excitation light beam 18. The first lens 28 is a converging collimating lens which collects the fluorescent light. It is preferably chosen with a large diameter so that it collects as much of the fluorescent light 26 as possible. The converging collimating lens 28 is positioned and aligned such that its focal point is exactly at the point of emission of the emitted fluorescent light 26. The fluorescent light 26 therefore comes out of the converging collimating lens 28 as parallel rays.

A second lens 30 upon which the parallel rays of light exiting from the converging collimating lens 28 impinge and a third lens 32 operate together to reduce the diameter of the beam of parallel rays of fluorescent light 26 output by the converging collimating lens 28 so that the resultant beam contains parallel rays and has a diameter that is compatible with the entrance aperture of the acousto-optic tunable filter 34. The use of those two lenses 30 and 32 is important because the entrance aperture of the acousto-optic tunable filter 34 is small, typically on the order of 3–7 mm and it is desirable to pass as much of the collected fluorescent light as possible through the acousto-optic tunable filter 34. The lens 30 is preferably a converging lens while the lens 32 is preferably a diverging lens such that their combined effect is to reduce the beam of light emerging from the converging collimating lens 28 by approximately the ratio of the focal length of the converging lens 30 and diverging lens 32.

The fluorescent light collected by the converging collimating lens 28 then enters the acousto-optic tunable filter 34 in order to be wavelength filtered. The acousto-optic tunable filter 34 may be an Acousto-Optic Tunable Filter available from Crystal Technology, Inc. of Palo Alto, Calif.

The acousto-optic tunable filter 34 is an electrically tunable optical filter which acts as a controllable optical wavelength filter such that a desired wavelength of light can be passed through the filter while all other wavelengths are blocked. Such acousto-optic tunable filters can be implemented by an optically birefringent crystal, such as tellurium dioxide ($TeO_2$) in which an acoustic wave is launched into the crystal to create an interaction between the acoustic wave and the light passing through the crystal.

The compression and rarefractions of the crystalline material due to the launched acoustic wave causes a diffraction grating-like effect to take place throughout the volume of the crystal. The optical wave whose wave vectors satisfies the wave matching condition with the acoustic wave is accumulatively diffracted and exits the crystal at a different angle from the rest of undiffracted light. Using such a device, a suitable arrangement of stops and apertures can be utilized to select a desired wavelength that has been diffracted for detection and subsequent processing. Since the acoustic frequencies utilized with such devices are in the range of tens to hundreds of megahertz in frequency, those waves can be established very quickly, on the order of microseconds or less. Such acousto-optic tunable filter devices are therefore capable of rapid wavelength tuning.

A second type of optical filter utilizes pneumatic liquid crystals whose birefrengence may be altered by varying the electric field that surrounds them. That has the effect of controlling the long chain-like molecules which in turn alters their birefrengence. That electric field can be established and controlled by varying a voltage applied to a parallel plate which contains the liquid crystals. An optical filter is created by using several zones of liquid crystals in order to implement a Lyot interferometer.

The acousto-optic tunable filter 34 is tuned using a digital synthesizer 36 which creates a radio frequency signal which corresponds to the desired optical wavelength to be analyzed at each moment in time. The output from the digital synthesizer 36 is amplified by a radio frequency amplifier 38 such that the power output from the digital synthesizer 36 is increased to approximately 0.5 to 1.0 watt. The amplified radio frequency signal is then fed from the output of the radio frequency amplifier 38 to the control input of the acousto-optic tunable filter 34. Light at the selected wavelength then exits from the acousto-optic tunable filter 34 at an angle of approximately 7 to 10 degrees from the rest of the light beam at 42.

The selected light 40 and 44 from the acousto-optic tunable filter 34 is diffracted in both directions relative to the main beam 42 leaving the acousto-optic tunable filter 34. The two diffracted beams 40 and 44 differ in polarization from one another. Each or both of the diffracted beams 40 and 44 at the selected wavelength can be detected by light detectors to provide a measurement of the fluorescent emissions of the DNA fragments at the selected wavelength. For the purposes of illustration, only a single detector 46 which is positioned to detect the diffracted light beam 44 is shown in FIG. 1.

The diffracted light representative of the fluorescent emissions which emerges from the acousto-optic tunable filter 34 can be detected by various types of devices, such as a photomultiplier which is cooled to decrease its noise background, or by a solid-state detector such as a PN junction or PIN diode. The detector should have good sensitivity with low noise characteristics in order to accommodate the low signal levels to be detected while at the same time it should be relatively fast to keep up with the speed that acousto-optic tunable filters can be scanned in order to realize the potential of the automated DNA sequencing system of the present invention.

The output from the detector 46 is fed to a computer 50 through a suitable interface device, such as an analog-to-digital converter (not shown) interface to the computer 50. Prior to supplying its output to the computer 50, the output from the detector 46 is electrically filtered using filter 48 in order to optimize the signal-to-noise ratio of the measured fluorescence value without degrading the speed of response of the system.

The computer 50 or an equivalent logic implementing unit, commands the logic and operation of the DNA sequencing system and also records the measured fluorescent data. The computer 50 is also connected to the digital synthesizer 36 in order to control the generation of the radio frequency signal which corresponds to the desired optical wavelength to be analyzed. The computer 50 may be an IBM or compatible type AT or more powerful personal computer equipped with appropriate memory, hard and floppy disk drives, video monitor and other peripherals. Preferably, the computer 50 may be formed from a microprocessor or microcontroller having the appropriate memory, computing power and other characteristics.

The computer 50 operates the instant automated DNA sequencing system by repeating a series of measurements of fluorescent data at a multiple number of wavelengths. The entire spectrum of fluorescence emissions from all four fluorescent tags can then be measured at any number of wavelengths under command from the computer 50. Preferably, a minimum of four different wavelengths are utilized, one wavelength centered on the emission of each fluorescent molecule, to a maximum of as many wavelengths as are desired which may, as a practical matter, have an upper limit of approximately 20 individual wavelengths per each fluorescent molecule.

The fluorescence emissions measured at each of the selected wavelengths can be defined as a data record. The computer 50 steps the acousto-optic tunable filter 34 to each of those wavelengths in turn and records the amount of fluorescent light detected at the detector 46. That information is stored in the non-volatile memory of the computer 50. When one record or measurements is completed, time-stamped and then recorded in the memory of the computer 50, the next record may then be measured immediately, or a small time delay may be implemented in order to avoid generating too much data too quickly. The process of recording records of fluorescent data continues until the run of the migrating DNA fragments contained within the pair 10 of parallel glass plates is complete.

As discussed previously, the float glass plates 10 utilized to contain the gel 12 emits fluorescence in the visible light wavelength range which can sometimes create problems in accurately detecting the fluorescence emissions 26 given off as a result of the stimulation of the DNA fragment 16 by the laser light beam 18. A more elegant and effective method for reducing or eliminating this background fluorescence is to utilize a second acousto-optic tunable filter or acousto-optic modulator to chop the laser light before the laser light impinges on the gel to stimulate the fluorescence molecules. Such a method allows electronic modulation of the stimulation and provides a mechanism for accomplishing synchronous detection or matched filter detection of the light at the detector. This greatly increases the rejection of the background fluorescence emitted by the float glass. An acousto-optic modulator, which is similar to the acousto-optic tunable filter, is designed to only pass or not to pass the light and is used essentially to turn the light on or off under electronic control.

A matched filter arrangement can alternatively be utilized where the stimulation laser light is modulated with a signature by use of an acousto-optic tunable filter and acousto-optic modulator and the matched filter response only to a signal that matches that signature. Such techniques take advantage of the operating characteristics of acoustic-optic tunable filters. On the other hand, prior art spinning filter wheels provide no control over those signal properties and, as a practical matter, operate far too slowly to be of much use to eliminate this background fluorescence.

Figure 4:
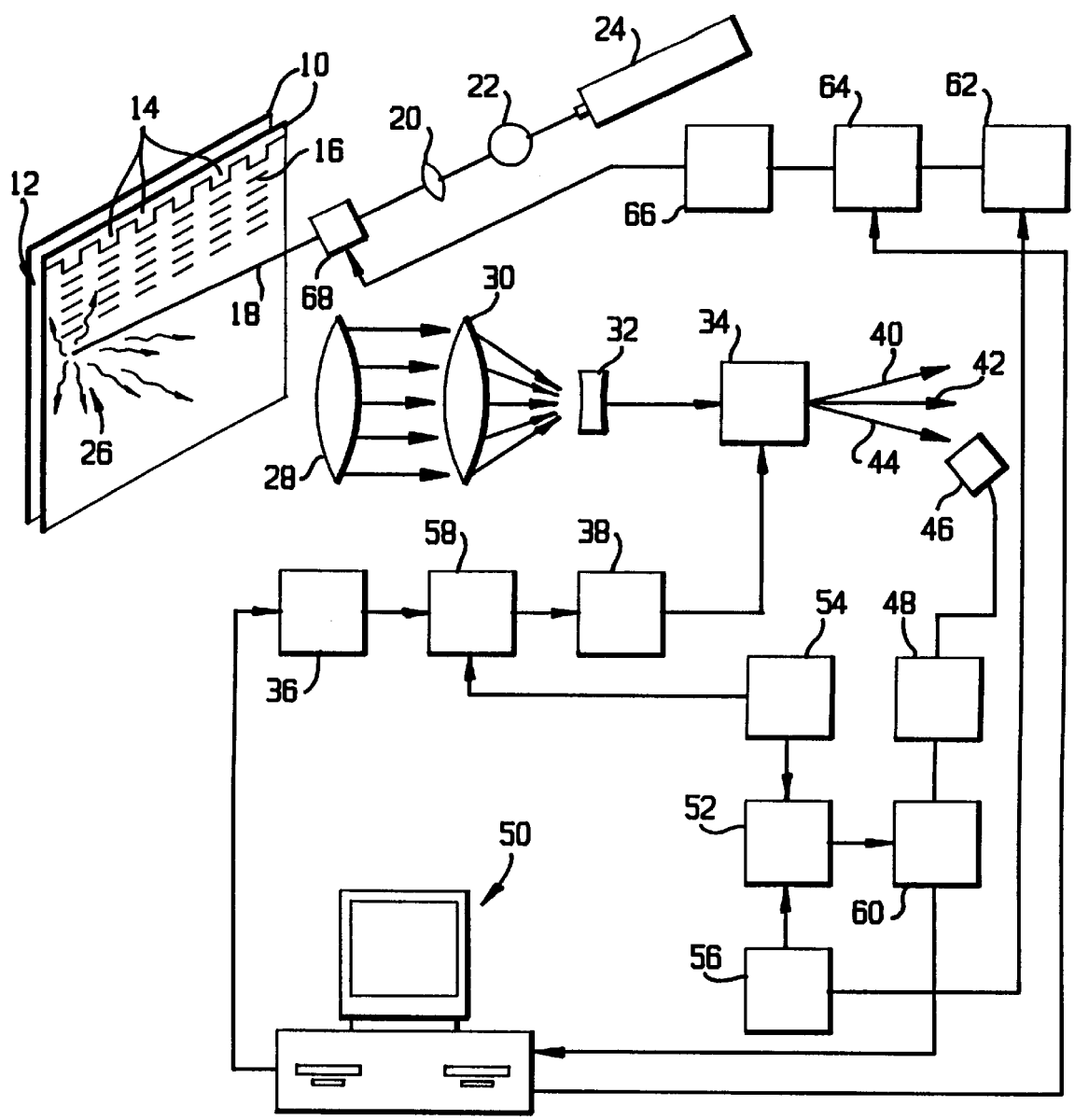
FIG. 4 is a block schematic diagram showing an alternate and preferred embodiment of the apparatus of the present invention.

Turning now to FIG. 4, there is shown a block schematic diagram of an altered and preferred embodiment of the apparatus of FIG. 1. The apparatus shown in FIG. 4 provides increased rejection of unwanted background fluorescence as well as stimulating fluorescence tags at their optimum wavelength in order to reduce stimulation of undesired fluorescence tags.

In the embodiment of the invention shown in FIG. 4, an acousto-optic tunable filter 68 is inserted in the path of the laser beam 18 prior to the laser light beam 18 impinging upon the DNA fragments 16. The acousto-optic tunable filter 68 is controlled by means of a digitally controlled radio frequency synthesizer 62 whose output is connected to a chopping or modulating circuit 64. The output from the chopping or modulating circuit 64 is amplified by means of the radio frequency power amplifier 66 which then feeds its output to the input of the acousto-optic tunable filter 68. The acousto-optic tunable filter 68, the digitally controlled synthesizer 62 and the radio frequency power amplifier 64 may be the same elements as described in connection with the first acousto-optic filter 34, the digital synthesizer 36 and the radio frequency amplifier 38 shown in both FIGS. 1 and 4 and as described in more detail in connection with the description of FIG. 1. The modulating or chopping circuits 64 are controlled by means of the digital oscillators or waveform generators 54 and 56, respectively.

The digital oscillators or waveform generators 54 and 56 generate a pulse waveform at separate frequencies that feed into the chopping circuits. Each chopping frequency is selected for optimum rejection based upon the fluorescent time constant, detector response times and system throughput requirements. The digitally controlled radio frequency synthesizer is connected to and controlled by the computer 50 such that the second acousto-optic tunable filter 68 is commanded to pass only the optimum stimulation wavelength for the fluorescent tag being stimulated at any moment in time.

The signal that is fed into the acousto-optic tunable filter 68 (or alternatively, an acousto-optic modulator) to modulate the laser beam 18 can also be fed into a synchronous detection circuit in order to implement a technique which is essentially the same as a phase-locked amplifier. The chopping signal can be phase adjusted as it enters the detection circuit so that the signals from the fluorescent tags are in phase with the chopping signal. The synchronous detection circuit then amplifies only signals that are matched in phase with the chopping signal. Such a scheme amplifies the wanted signal, the DNA tags, while not amplifying the unwanted signal from the fluorescence caused by the float glass.

In addition, the first acousto-optic tunable filter 34 can also be chopped and the detection function of the apparatus of FIG. 4 can be doubly synchronous in order to provide a still further rejection of unwanted signals. By properly utilizing the acousto-optic tunable filter 68 through which the laser beam 18 passes, the optimum stimulation wavelength for each fluorophore can be selected in turn in order to provide its stimulation when it is desired to measure that fluorophore. That reduces the emission of fluorescence from the other tags by not stimulating them at their optimum wavelength. The rejection of unwanted signals is important because the desired signal being measured is very small in comparison and precise detection is important for the performance of the inventive apparatus. As discussed earlier, LI-COR, Inc. utilizes a fluorophore that emits in the near infrared wavelength range which eliminates the fluorescent emissions of the float glass. The present invention can be utilized with all wavelength ranges of fluorescent emissions by the fluorophores by selecting the desired acousto-optic tunable filter that operates in the wavelength range of the fluorescent emissions to be detected. The acousto-optic tunable filter technology readily works in the infrared range in order to be able to handle the fluorophores utilized by LI-COR, as well as those utilized by others.

In order to provide the double synchronous function, a second chopping circuit 58 is inserted between the digitally controlled synthesizer 36 and the radio frequency power amplifier 38 that chops or modulates the signal output by the digitally controlled synthesizer 36 prior to its amplification by the radio frequency power amplifier 38. The second chopping circuit 58 is commanded by the first digital oscillator or waveform generator 54 while the second chopping circuit 64 is commanded by the second digital oscillator or waveform generator 56. The digital oscillators or waveform generators 54 and 56 generate a pulse waveform at separate frequencies that are fed to respective chopping circuits 58 and 64. Each chopping frequency is selected for optimum rejection based upon fluorescent time constants, detector response times and system throughput requirements.

By adding the digital oscillator or waveform generator 54 and the chopping circuit 58, as described above to the circuitry of FIG. 1, the light received at the detector 46 is modulated in a distinct manner only unto the light at the wavelength that the acoustic-optic tunable filter 34 is selecting at any moment of time. When that light is detected in synchronism with its chopping source, as described herein, a large processing gain is realized which amplifies only the desired selected light and rejects all other light.

By adding the digital oscillator or waveform generator 26 and the second chopping circuit 64 to the circuitry shown in FIG. 1, the light exiting from the acousto-optic tunable filter 68 that impinges on the gel 12 has a distinct signature at the chopping frequency of the waveform generator 56. When synchronously detected, only light from the fluorescence tags stimulated by the chopped excitation source will be amplified and all other light will be rejected to a great extent.

The combiner 52 is used to combine the chopping signals generated by the waveform generators 54 and 56 in order to create a signal that is fed into the synchronous detector 60. The combination of the outputs from the two chopping sources 54 and 56 that are of separate frequencies in order to create one combined chopping signal which is fed into the synchronous demodulator 60, permits only the light that has been processed through both of the acousto-optic tunable filters 34 and 68 to be effectively amplified. That produces the result of rejected the unwanted background fluorescence and other extraneous light from being amplified. The desired light from the fluorescence molecule at interest at any moment in time is therefore greatly amplified over any other light or noise that may enter the detector 46.

As is known to those of ordinary skill in the art, synchronous demodulators such as element 60 are known in the art and are alternatively termed phased-locked amplifiers when used with appropriate reference signals. While synchronous detection has been suggested in the art for use with acousto-optic tunable filters, the use of dual chopping sources and the combination of their chopping signals in order to synchronously detect a signal from a detector which has light entering it from two acousto-optic tunable filters used in this manner to detect fluorescent tag on DNA is new and novel.

In the event that the selection of a different wavelength for the stimulation light for each fluorescent tag is not needed, than the acousto-optic tunable filter 68 can be replaced with an acousto-optic modulator which does not need the second digitally controlled radio frequency synthesizer 62 nor the software operating on the computer 50 that controls the operation of that radio frequency synthesizer 62. A fixed radio frequency is generally used with an acousto-optic modulator such that it is switched on and off at the desired chopping frequency.

Figure 2A:
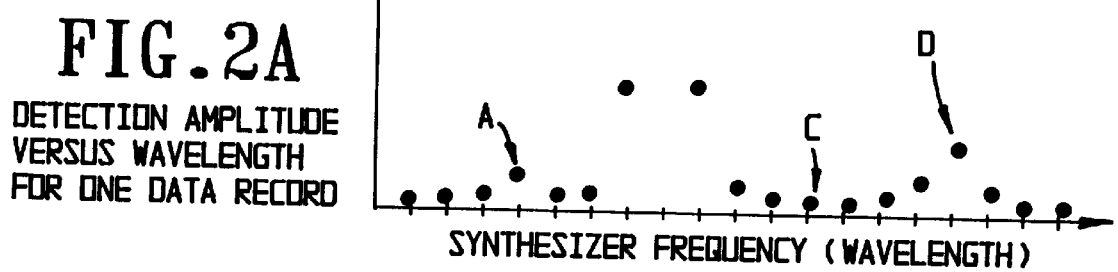
FIG. 2A is a drawing of a graph of a data record showing the detection amplitude versus the wavelength for a single data record.
Figure 2B:
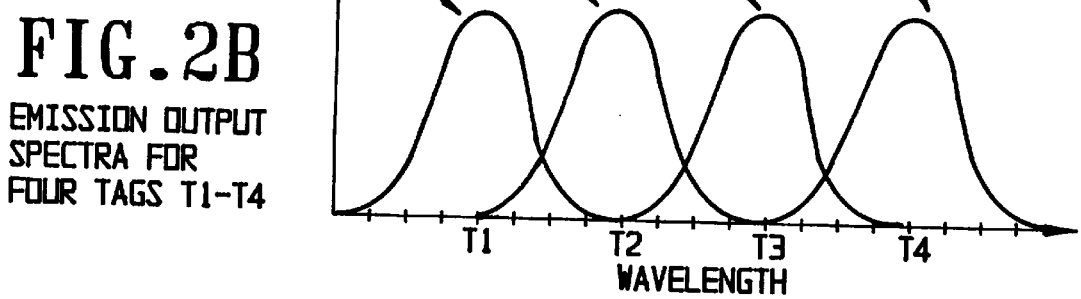
FIG. 2B is a drawing of a graph illustrating the emission output spectra for Tags T1–T4 for the data record of FIG. 2A.

FIGS. 2A and 2B show a typical record of data generated by the automated DNA sequencing system of the present invention. FIG. 3 illustrates the band data generated from the data record shown in FIGS. 2A and 2B that represents the progression of bands down the polyacrylamide gel 12. As a band of tagged fragments comes to the point of detection where the laser beam 18 excitation spot is focused, a rise in the signal at the characteristic wavelength for that fluorophore is observed.

FIG. 2A illustrates various data points within a graph of the detection amplitude synthesizer frequency or wavelength for each of the four fluorophores and forms one data record. The data in this graph indicates at data point A, a small detection signal from the Tag T1 showing a band tail. Data point B indicates a strong detection signal from the Tag T2 showing a band peak. Data point C indicates that no detection signal was detected from the Tag T3, showing that there is no band present. Data point D indicates a small detection signal from the Tag T4 showing a band tail.

FIG. 2B is a graph showing the emission output of the detected fluorophore spectra versus its wavelength for the four tags T1–T4. Each of the curves E–H corresponds to the emission spectrum for the Tags T1–T4, respectively.

The data consisting of records of measurements at the selected number of wavelengths is processed in a number of steps in order to determine a DNA sequence. First, each record of data is evaluated in order to determine the amount of each fluorophore present at the point of detection at the point and time that the record was recorded. That is done by fitting the spectral emission curve of each fluorophore to the data. Alternatively, a method which consumes less computer processing power would be to determine the ratio of signal strength at the peak of each fluorophore's emission to the signal strengths at the valleys between the emissions. In any event, whatever method is utilized, a value of the amount of fluorophore present is determined for each of the four possible fluorophores in the gel 12 for each record of the entire data set. In order to aid in processing, four separate data sets are then created. Each of those data sets represents the amount of one fluorophore present at the time of each record of initial data. That data set is depicted in FIG. 3.

FIG. 3 illustrates the detection amplitude versus the record number for each of the tags T1–T4. Data point I of FIG. 3 shows a band peak at the record number 6 for the Tag T1, which represents the base A. Data point shown J shown in FIG. 3 indicates a band peak at the record number 24 for the TAG T1, which represents the base A. The reference letter K indicates the base sequence determined by the data shown, namely AGCTAC.

The emission spectrum of each fluorophore is known in advance with respect to its center frequency, lineshape, linewidth, and percent effect. A software program is S used to implement a least-squares fit of each of these line shape functions to the data collected to determine the amount of each fluorophore present at each instant of time. Suitable software products are readily available to perform this function. In practice, this procedure is performed at a rate that is determined by the speed of the detection electronics, consistent with the needed signal-to-noise ratio of the detected signal and the processing power of the computer 50. Several times a second to once every few seconds are preferred rates due to the slow speed of migration of the fragments.

Obtaining a spectral scan of the fluorophore present and matching the known lineshapes to the collected data is a useful technique for measuring the amount of fluorophore present at each point on the gel 12. When the bands 16 get crowded together as the fragments get longer, there is a significant overlap of the bands 16 due to the diffusion effects of migration. The data collected by the spectral scan allows a second processing to be implemented that provides significantly increased band position determination.

Each band is spread out in space along the direction of migration through the gel 12. That is a consequence of the statistical nature of migration. With the prior art crude detection ability, the ability to resolve which band is ahead of the other was limited when the leading edge of one band began to overlap with the trailing edge of the band ahead of it. At that point, the bands became too blurred together and the sequence could not be determined any further.

The next processing step of the present invention is to perform at least squares fit of a band diffusion function to the data collected in the previous step. That is done for each fluorophore so that the band centroid, or center position of each band, can be determined with a known amount of statistical certainty. The bands 16 are then ranked in order of progression until they are separated by an amount that is within a given tolerance of the computed position certainty. At that point, the present invention ends. A significant improvement in DNA sequence determination capability is realized if even 50 or 100 more bases are determined by the present invention over existing techniques.

After the positions have been assigned on the gel for each band on each of the four data sets of the four fluorophores, the DNA sequence may be determined by inspecting the data set and observing which fluorophore is next in progression along the gel 12. The DNA sequence is then called out in this fashion until the position in adjacent bands becomes less than the computed position uncertainty for the bands.

The band diffusion function is determined by analysis or through the laws of diffusion to obtain a mathematical function that the detected fluorophore data can be fitted to. Alternatively, a Gaussian function can be used as a good approximation to the distribution of fragments in the band 16. Data from a number of bands 16 in the same vicinity are used to determine a band to band separation in a given portion of the gel 12, and a band separation decrease per base. That creates a situation similar to establishing a timing track for bases along the gel, in a manner analogous to synchronous detection of digital data from a communication link with added noise and disturbances. Once those relations are computed from the collected data, the determination of the band sequence becomes more accurate because one of the possible four bases must exist at each timing mark and a statistical prediction can be made. That continues until the statistical probability of accurately determining which base is next in the sequence becomes unacceptably low to the researcher. The researcher can then make his own choice as to when to stop the analysis because the algorithm gives the statistical level of confidence for each base analyzed.

Figure 5B:
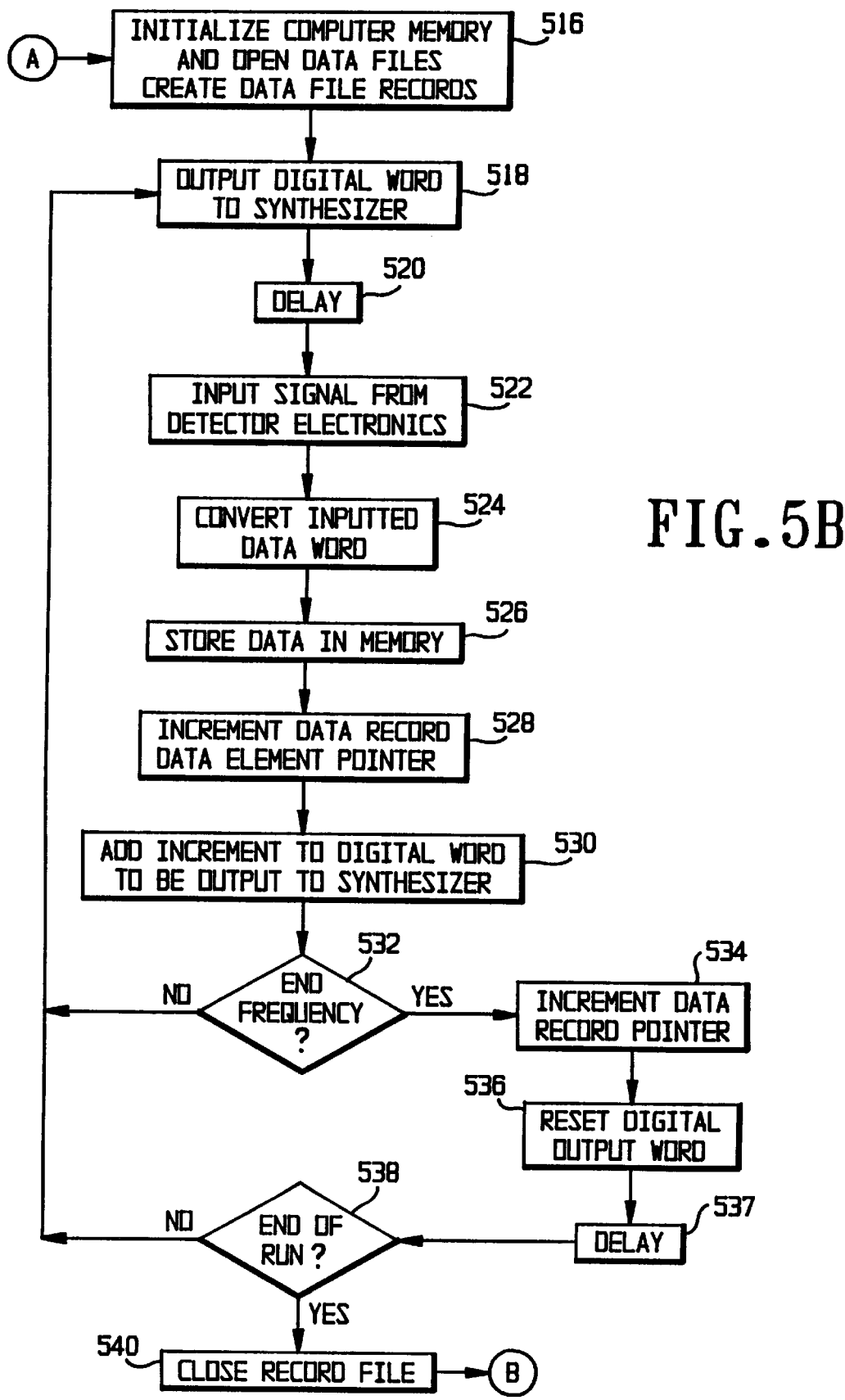
FIG. 5B is a diagram of a flow chart of a portion of the DNA sequencing software used for collecting band data in connection with the operation of the apparatus of the present invention.

A diagram of the flow chart of the DNA sequencing software used in connection with the preferred embodiment of the present invention is shown in FIGS. 5A–5D. Referring first to FIG. 5A, there is shown, in flow chart form, a first portion of the DNA sequencing software used in connection with the present invention for entering the initial input parameters. At step 500, the start and end wavelengths for the digitally controlled radio frequency synthesizer 62 are input. Then, the number of wavelength steps is input at step 502. The minimum number of wavelength steps is 4, one for each florescent tag, however the maximum number may be as high as 20. The maximum or upper limit of the number of wavelength steps is determined by such factors as the wavelength resolution of the optical system being utilized, the data processing demands imposed by taking more data points and the point of diminishing return with respect to determining the line shape of each florescent tag emission.

Next, at step 504, the amount of pause or delay between data records is inputted. A delay is needed because the optical techniques used in connection with the present invention are much faster than the migration of the DNA fragments in the gel. Therefore, a delay of about 0.01 to approximately 3 seconds will be necessary between taking data records in order to not generate an amount of data that cannot be handled or that is redundant. The amount of the delay is also a function of how fast the bands run down the gel or capillary, which will in turn depend on parameters of the testing such as the voltage used. In general, the advantage of the present invention is in its ability to allow the process to run as fast as it possibly can in order to improve the overall throughput of DNA sequencing.

Utilizing the start and end wavelengths and the number of wavelength steps inputted in steps in 500–504, the start frequency, end frequency and frequency increment are computed at step 506 for the digital synthesizer 62. A synthesizer frequency needed to select a desired optical wavelength is computed from the characteristics of the optically non-linear material that the acousto-optic tunable filter is made from, which is known in the art.

It should again be noted that it is desirable to utilize a digital synthesizer in the preferred embodiment of this invention. However, an analog-based frequency generator can also be utilized, based upon a voltage controlled oscillator in which the controlling voltage is swept with a ramp generator. In that event, that start voltage, end voltage and voltage ramp rate would replace the start frequency, end frequency and frequency step information input in steps 500–502.

FIG. 5B shows in flow chart form the collect band data or data acquisition portion of the DNA sequencing software utilized in connection with the present invention. The software causes a digital word to be outputted to the digital synthesizer in order to command the synthesizer to the desired frequency through a standard output port or in a manner prescribed by the interface between the computer 50 and the digital synthesizer 62. It will be obvious to those of ordinary skill in the art that there are many ways of achieving that function known in the art. It will also be obvious that utilizing a stand-alone personal computer for the computer 50 is only an example of a computer which can be used in connection with this invention. Obviously, any type of digital processing unit, such a microprocessor, microcontroller or other type of computer would also adequately serve the same function.

As shown in FIG. 5B, at step 516, the computer memory is initialized and data files are opened. A file of data records is created, in which each data record has a data element used to store the detector output at each frequency. That data is stored in the format chosen for data processing. Therefore, there are from 4 to 20 data elements for each data record and the file of data records would be as long as the data run requires, typically thousands of data records. In addition, a data record counter and pointers to the data record file are initialized and the first word to the digital synthesizer 62 is generated. The first word to the digital synthesizer 62 is the word that commands the synthesizer to select the start wavelength on the florescence spectrum. The software prepares to output that word, and then goes to step 518.

At step 518, the DNA sequencing software outputs the first digital word to the synthesizer, which commands the synthesizer 62 to move to the frequency of the wavelength desired at that point in time. The program then waits for a small delay at step 520 for the electronics to settle and for the signal generated by the detector electronics to stabilize. That delay is typically from a few to a few hundred microseconds.

At step 522, the signal from the detector electronics is input into the DNA sequencing program by means of an analog-to-digital converter interfaced to the computer 50. The inputted data word from the detector electronics 46, 48 is converted at step 524 into a convenient internal format for data analysis, such as a floating point format. The data word is then stored in the computer memory at step 526 in a data record at the element number associated with that particular frequency step. The data record data element pointer is then incremented by one at step 528 and a frequency increment is added to the present frequency to be output to the digital synthesizer 62 at step 530.

At step 532, a determination is made of whether the frequency to be output to the digital synthesizer 62 as generated at step 530 is the end frequency. If a negative determination is made at step 532, then the program returns to step 518 and outputs the current digital word (frequency) to the digital synthesizer 62 and then continues on at step 520 as previously described.

If an affirmative determination is made at step 532, that means that a data record has been completed. In that event, the data record pointer is incremented at step 534 and the digital output word is reset to the selected start wavelength at step 536. Then, the software waits for a period of time at step 537 equal to the delay inputted at step 504.

Figure 5C:
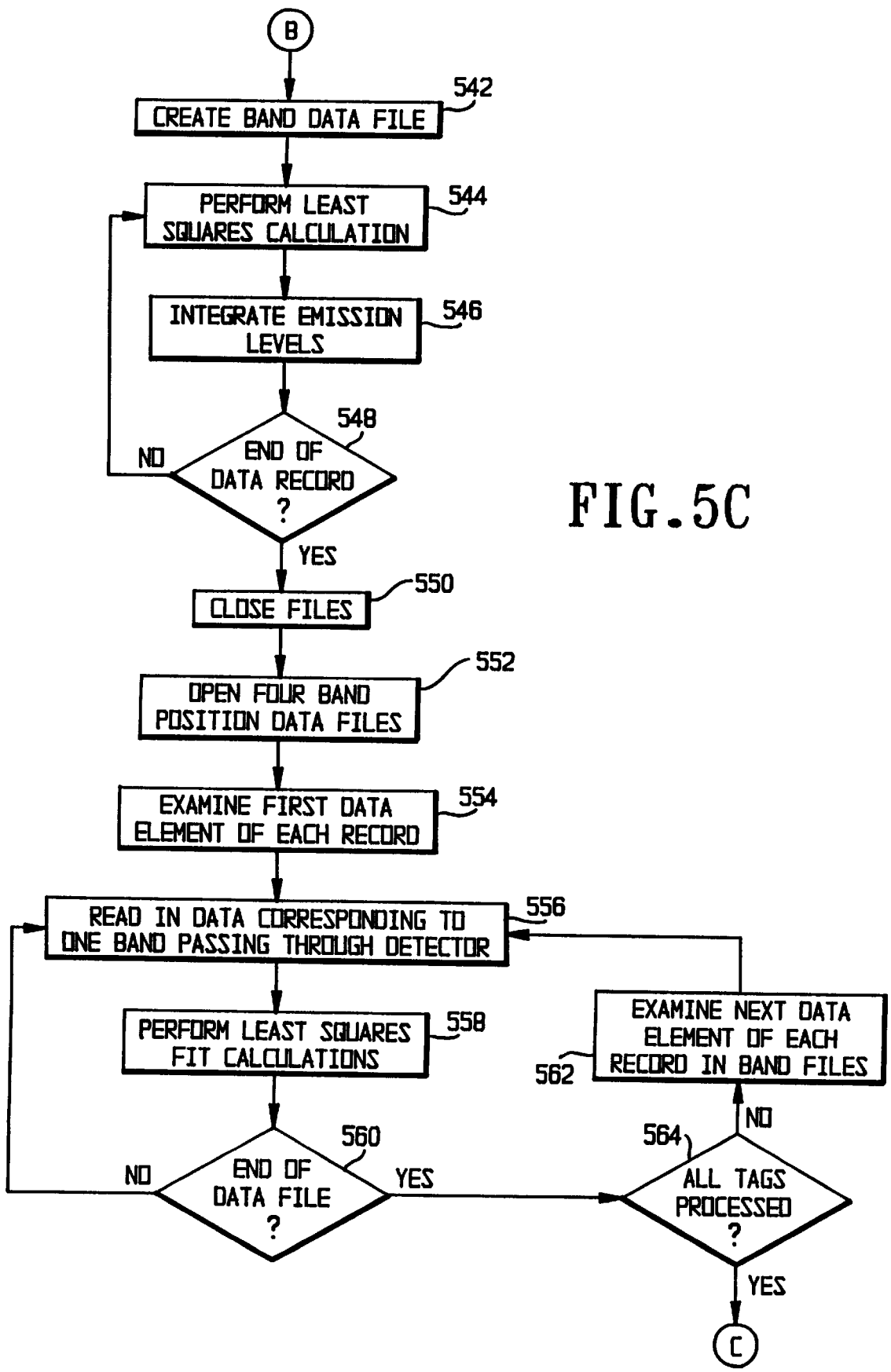
FIG. 5C is a diagram of a flow chart of a portion of the DNA sequencing software relating to analyzing data records and band data used in connection with the apparatus of the present invention.

After the delay at step 537, a determination is made of whether the end of the run has been reached at step 538. If a negative determination is made at step 538, then the program returns to begin repeating the steps described above, beginning with step 518. If an affirmative determination is made at step 538 then the record files are closed at step 540 and the software proceeds to analyze the data records and band data, the flow chart of which is shown in FIG. 5C. [John-please examine steps 532–540 closely to determine that the flow chart is correct]

The object of the portion of the DNA sequencing software which analyzes the data records is to use the data in each of the data records to determine the amount of florescent tag present of each tag in the sample of DNA fragments at the time that each data record was taken. Curve fitting algorithms of the resonance line shaped function, sometimes termed Lorentzian, or of the common bell shape curve, termed Gaussian, are used to obtain the parameters of line position, width and height for each florescent tag in the sample for each data record in the data file. Methods for performing that curve fitting are well known in the art.

At step 542, a band data file is created which contains the records of data of the band concentration for each florescent tag. Each record in that file contains a data element representing the amount of florescent tag present for each tag in the sample of DNA fragments. Since there are typically 4 tags, there will be 4 data elements per data record. Step 542, the band data file pointers are initialized, the data record file is opened and the pointers for the opened data file are initialized.

Then, at step 544, for each record of the data record file accumulated in step 542, a least squares fit of a curve containing a height, width and position for each florescent emission in the DNA samples is performed. At step 544, a value is obtained for the height, width and position for the emission of each florescent tag in the data record.

At step 546, for each emission line, the emission level is integrated over the span of the data record in order to obtain a value of the total emissions for each florescent tag. That value is stored in the data element for that florescent tag in the corresponding record of the band data file.

A determination is then made, at step 548, of whether the end of the data record has been reached. If a negative determination is made at step 548, then the program returns to step 544 and continues to execute from that point until each data record has been processed to obtain a value of the total emission for each florescent tag at each data record initially recorded.

If an affirmative determination is made at step 548, then all of the files are closed at step 550 and the program proceeds to the analyzing of band data portion of the DNA sequencing software, the flow chart of which is shown in steps 552–564.

After executing step 550, a data file of band data representing the concentration of each florescence tag at each point in time that data was recorded has been generated. By analyzing data for a single florescent tag, the data will reveal a series of rises and falls that resemble a sequence of humps or hills. Those are the bands with that tag passing by the detector in time. A position is then assigned to the center of each those hills or bands for each of the four florescent tags. A least squares curve fitting process is used with a Gaussian line shape in order to determine the center position.

At step 532, four band position data files are opened. Each data file consists of records with two data elements, one representing the position and the other representing the position uncertainty of each band. Also, data pointers and record counters are initialized.

The first data element of each record in the band data file is then examined at step 554. That data element represents the concentration of the first florescent tag at each point in time.

At step 556, the data corresponding to one band passing through the detector is read in. That data is determined by a coarse examination of the data to discern a peak and a valley in the data. Then, a least squares fit of that section of data to the Gaussian curve is performed at step 558. The center position, width, height and position uncertainty is calculated from that fit and recorded in the corresponding data record.

A determination of whether the end of the data file has been reached is then made at step 560. If a negative determination is made at step 560, then the program returns and begins executing again starting with step 556.

If an affirmative determination is made at step 560, then the next data element in the band file is examined at step 562 and the data corresponding to that band passing through the detector is then read in at step 556 such that the processing of the next florescent tag is performed.

Prior to reaching step 562, after an affirmative determination at step 560, a determination is made at step 564 of whether all of the florescent tags have been processed. If a negative determination is made at step 564, then step 562 is executed. If an affirmative determination is made at step 562 then the DNA sequencing software program proceeds to the next processing step of calling bases. [John-please check steps 554–564 of FIG. 5C to determine that I have accurately drawn then on the flow chart]

When the DNA sequencing software program reaches the calling bases portion of the program, the flow chart of which is shown in FIG. 5D, four data files that contain positions of bands for their respective florescence tags have been generated. While this portion of the DNA sequencing software can be implemented in numerous ways, it is important to note that this portion of the DNA sequencing software is able to perform its function due to the ability of the acousto-optic tunable filters to generate data which is good enough to allow the structure of the florescence data coming from multiple florescence tags to be utilized to obtain good measurements of each flourophore and the precise center position of each band.

The determination of the base sequence of the fragment of DNA being analyzed is performed as follows by the DNA sequencing program utilized in connection with the operation of the present invention.

At step 508, the band position data files are examined. The first data record in each file is looked at. The file whose band arrived first, or that has the closest position to the start is determined to be the first base in the sequence. That is declared a valid base call if the position of uncertainty between that base and the next closest one does not suggest that those two bases overlap. If there is a suggestion that they overlap, the sequence has been determined to the maximum extent possible. Therefore, that is the end of the sequence determination.

At step 510, the base being examined is taken out of the data file and the remaining bases in that base file are shifted down by one so that the next base in that file takes the place of the first base that has been called out. A determination is then made at step 512 of whether the end of the data has been reached. If a negative determination is made at step 512, meaning that all of the bases have not been called out, then steps 508 and 510 are repeated again. If an affirmative determination is made at step 512, then the DNA sequencing software ends at step 514.

As will be obvious to those of ordinary skill in the art, there are many alternate methods by which to determine the sequence in which the bands arrived at the detector. Any method that examines the band position data and determines which band arrived first, then second, and so forth, will properly determine the base sequence of the DNA fragment.

Although the foregoing describes the basic steps for processing the data produced by the automated DNA sequencing system of the present invention, many enhancements may be made to the processing steps. In addition, for purposes of clarity, a few well-known details have been omitted. Such details would include, for example, subtracting background noise, correcting for the relative fluorophore emission strengths, correcting for the relative fluorophore migration rates, removing the fluorescence emissions produced by the glass plates 10 or the gel 12 themselves, removing the Raman scattering line from water, as well as a few other extraneous factors. However, such details do not alter the operation of the disclosed automated DNA sequencing system.

As has been described previously, some automated DNA sequencing systems utilize a single florescence tag because of the difficulty in accurately measuring the amount of each tag present when performing multiple florescence tag sequencing. The problem arises due to the overlapping spectral output of the florescent emissions which makes the signal of one florescence molecule ride of the skirt of an adjacent one. That in turn gives rise to errors in the determination of the quantity of each florescence tag present.

If a band of DNA consisting of fragments labeled with one florescence molecule happens to follow closely behind a band tagged with another molecule, as will often happen, the emissions of the previous band will tend to raise the optical detection baseline for the measurement of the present band. Such effects will cause errors in the measurements and make the technique break down sooner than could be realized with the present invention disclosed herein. Thus, the use of the present invention with a single florescence tag will likewise provide an increase in speed of DNA sequencing.

Also, as briefly described herein, capillary methods for sequencing DNA fragments may be utilized in place of flat gel techniques. The apparatus of the present invention will operate in a similar manner when used with capillary methods instead of flat gel apparatus. The capillaries appear as a strand of material and the mixture of tagged DNA fragments are introduced at one end. The fragments are made to travel along the strand and will separate in size, with the shortest fragments travelling faster than the longer ones. The capillary methods techniques can be thought of as a thin strand of material that the tagged DNA fragments are being made to travel through instead of the flat gel.

Band separation in the strand occurs in a manner analogous to that which occurs when using the flat gel techniques. Excitation laser beam and detection optics are then focused on a point on the strand and the passage of the bands is measured in a manner similar to that with a gel.

Although only a preferred embodiment is specifically illustrated and described herein, it will be appreciated that many modifications and variations of the present invention are possible in light of the above teachings and within the purview of the appended claims without departing from the spirit and intended scope of invention.

What is claimed is:

1. Apparatus for automatically sequencing a plurality of DNA fragments, each of said plurality of DNA fragments having a different base being tagged with a different fluorescent tag which can be caused to emit fluorescent light having a different characteristic wavelength corresponding to said different fluorescent tag comprising:

a light beam generator for generating a beam of light for stimulating the emission of light at its characteristic wavelength from each of said fluorescent tagged plurality of DNA fragments;

a means for optimizing the wavelength of said beam of light used to stimulate said emissions of light from said tagged plurality of DNA fragments;

a focussing element for receiving said emitted light from said tagged plurality of DNA fragments and forming a focussed light beam of substantially parallel rays of light;

a first acousto-optic tunable filter for receiving said focussed light beam from said focussing element;

a digital data processor for controlling said acousto-optic tunable filter such that said acousto-optic tunable filter is operated to diffract a predetermined portion of said received focussed light beam such that said diffracted portion of said focussed light beam exits said acousto-optic tunable filter at at least one angle separate from said focussed light beam; and a detector for receiving at least a portion of said diffracted portion of said focussed light beam exiting said first acousto-optic filter for generating an electrical representation of the fluorescent light emissions of said plurality of DNA fragments.

2. The apparatus of claim 1, wherein said digital data processor stores said electrical representation of said fluorescent light emissions for later analysis.

3. The apparatus of claim 1, wherein said digital data processor steps said first acousto-optic tunable filter through a plurality of wavelengths, wherein each of said plurality of wavelengths corresponds to a different characteristic wavelength of said fluorescent tagged plurality of DNA fragments.

4. The apparatus of claim 1, wherein said means for optimizing comprises a second acoustic-optic tunable filter through which said beam of light passes prior to stimulating said emission of light from said tagged plurality of DNA fragments.

5. The apparatus of claim 1, further including a second acousto-optic tunable filter for receiving said beam of light from said light generator and for modulating said beam of light prior to the stimulation of said emission of light from said tagged plurality of DNA fragments.

6. The apparatus of claim 5, further comprising:

a waveform generator for generating a waveform for causing said first acousto-optic tunable filter to modulate said focussed light beam; and a synchronous demodulator connected to receive said waveform generated by said waveform generator for synchronously detecting at least a portion of said diffracted portion of said focussed light beam exiting said first acousto-optic tunable filter.

7. The apparatus of claim 1, further including a waveform generator for generating a waveform for causing said first acousto-optic tunable filter to modulate said focussed light beam.

8. The apparatus of claim 7, further including a synchronous demodulator connected to receive said waveform generated by said waveform generator for synchronously detecting at least a portion of said diffracted portion of said focussed light beam exiting said first acousto-optic tunable filter.

9. Apparatus for automatically detecting a plurality of DNA fragments, each of said plurality of DNA fragments having a different predetermined characteristic being tagged with a different fluorescent tag which can be caused to emit fluorescent light having a different characteristic wavelength corresponding to said different fluorescent tag, comprising:

a light beam generator for generating a beam of light for stimulating the emission of light at its characteristic wavelength from each of said fluorescent tagged plurality of DNA fragments;

a means for optimizing the wavelength of said beam of light used to stimulate said emissions of light from said tagged plurality of DNA fragments;

a focussing element for receiving said emitted light from said tagged plurality of DNA fragments and forming a focussed light beam of substantially parallel rays of light;

a first acousto-optic tunable filter for receiving said focussed light beam from said focussing element;

a digital data processor for controlling said acousto-optic tunable filter such that said acousto-optic tunable filter is operated to diffract a predetermined portion of said received focussed light beam such that said diffracted portion of said focussed light beam exits said acousto-optic tunable filter at at least one angle separate from said focussed light beam; and a detector for receiving at least a portion of said diffracted portion of said focussed light beam exiting said first acousto-optic tunable filter for generating an electrical representation of the fluorescent light emissions of said plurality of DNA fragments.

10. The apparatus of claim 9, wherein said digital data processor stores said electrical representation of said fluorescent light emissions for later analysis.

11. The apparatus of claim 9, wherein said digital data processor steps said first acousto-optic tunable filter through a plurality of wavelengths, wherein each of said plurality of wavelengths corresponds to a different characteristic wavelength of said fluorescent tagged plurality of DNA fragments.

12. The apparatus of claim 9, wherein said means for optimizing comprises an acoustic-optic filter through which said beam of light passes prior to stimulating said emission of light from said tagged plurality of DNA fragments.

13. The apparatus of claim 9, further including a second acousto-optic tunable filter for receiving said beam of light from said light generator and for modulating said beam of light prior to the stimulation of said emission of light from said tagged plurality of DNA fragments.

14. The apparatus of claim 13, further comprising:

a waveform generator for generating a waveform for causing said first acousto-optic tunable filter to modulate said focussed light beam; and a synchronous demodulator connected to receive said waveform generated by said waveform generator for synchronously detecting at least a portion of said diffracted portion of said focussed light beam exiting said first acousto-optic tunable filter.

15. The apparatus of claim 9, further including a waveform generator for generating a waveform for causing said first acousto-optic tunable filter to modulate said focussed light beam.

16. The apparatus of claim 15, further including a synchronous demodulator connected to receive said waveform generated by said waveform generator for synchronously detecting at least a portion of said diffracted portion of said focussed light beam exiting said first acousto-optic tunable filter.

* * * * *